US012446766B2

(12) United States Patent
Bastia

(10) Patent No.: US 12,446,766 B2
(45) **Date of Patent: *Oct. 21, 2025**

(54) DEVICE FOR INSPECTING A CAVITY OF A PATIENT

(71) Applicant: THD S.P.A., Correggio (IT)

(72) Inventor: Filippo Bastia, Soliera (IT)

(73) Assignee: THD S.P.A., Correggio (IT)

( * ) Notice: Subject to any disclaimer, the term of this patent is extended or adjusted under 35 U.S.C. 154(b) by 470 days.

This patent is subject to a terminal disclaimer.

(21) Appl. No.: 18/047,038

(22) Filed: Oct. 17, 2022

(65) Prior Publication Data

US 2023/0130319 A1 Apr. 27, 2023

(30) Foreign Application Priority Data

Oct. 25, 2021 (IT) ........................ 102021000027314

(51) Int. Cl.
*A61B 1/32* (2006.01)

(52) U.S. Cl.
CPC ..................................... *A61B 1/32* (2013.01)

(58) Field of Classification Search
CPC .. A61B 17/0206; A61B 2217/002; A61B 1/31
USPC ................................................. 600/184–245
See application file for complete search history.

(56) References Cited

U.S. PATENT DOCUMENTS

| | | | |
|---|---|---|---|
| 1,849,701 | A | 3/1932 | Allyn |
| 4,905,670 | A | 3/1990 | Adair |
| 5,407,427 | A | 4/1995 | Zhu et al. |
| 5,458,595 | A | 10/1995 | Tadir et al. |
| 5,577,993 | A | 11/1996 | Zhu et al. |
| 6,572,631 | B1 | 6/2003 | McCartney |
| 9,693,729 | B1 | 7/2017 | Lash et al. |
| 10,463,244 | B2 | 11/2019 | Bastia |

(Continued)

FOREIGN PATENT DOCUMENTS

| | | | | |
|---|---|---|---|---|
| EP | 0645982 B1 | 2/2000 | | |
| EP | 3329834 A1 * | 6/2018 | ......... | A61B 1/00066 |

(Continued)

*Primary Examiner* — Eduardo C Robert
*Assistant Examiner* — Tara Rose E Carter
(74) *Attorney, Agent, or Firm* — Chrisman Gallo Tochtrop LLC

(57) ABSTRACT

Device for inspecting a cavity of a patient comprising a retractor body, extending along a longitudinal axis between a distal end and a proximal end, and a handle applied or fixed to the proximal end of the retractor body, and an adapter body.

The retractor body has a distal portion having a substantially tubular shape and a proximal portion extending from the distal portion in a diverging fashion, wherein the distal portion defines a retraction zone of an internal cavity of a patient and internally delimits an internal volume accessible from a rear access opening made on the proximal portion, wherein said distal portion of the retractor body has at least one front and/or lateral opening to allow access to the mucosa or tissue of the patient from said internal volume. Said adapter body being removably applicable, in use, to said retractor body and in particular to said proximal portion. The device further comprises at least one support seat arranged on the retractor body and configured to supportingly receive a front surface of a laser head.

16 Claims, 10 Drawing Sheets

(56) References Cited

U.S. PATENT DOCUMENTS

| | | | |
|---|---|---|---|
| 2003/0130559 | A1 | 7/2003 | Morin et al. |
| 2003/0225313 | A1 | 12/2003 | Borodulin et al. |
| 2004/0138525 | A1 | 7/2004 | Saadat et al. |
| 2004/0138529 | A1 | 7/2004 | Saadat et al. |
| 2005/0065397 | A1 | 3/2005 | Saadat et al. |
| 2005/0065401 | A1 | 3/2005 | Saadat et al. |
| 2005/0107663 | A1 | 5/2005 | Saadat et al. |
| 2005/0113640 | A1 | 5/2005 | Saadat et al. |
| 2005/0261714 | A1 | 11/2005 | McCartney |
| 2007/0112356 | A1 | 5/2007 | McCartney |
| 2008/0281204 | A1 | 11/2008 | Raffaele et al. |
| 2011/0046441 | A1 | 2/2011 | Saadat et al. |
| 2011/0071349 | A1 | 3/2011 | Drontle et al. |
| 2015/0031950 | A1 | 1/2015 | Drontle et al. |
| 2015/0282696 | A1 | 10/2015 | Sun et al. |
| 2018/0125350 | A1 | 5/2018 | Sias |
| 2018/0146849 | A1 | 5/2018 | Bastia |
| 2020/0107714 | A1 | 4/2020 | Bar-or et al. |
| 2020/0345212 | A1 | 11/2020 | Dreyer et al. |

FOREIGN PATENT DOCUMENTS

| | | | |
|---|---|---|---|
| EP | 3772322 | A1 | 2/2021 |
| GB | 2391815 | A | 2/2004 |
| IT | M020120177 | | 1/2014 |
| KR | 101386236 | B1 | 4/2014 |
| WO | 2010048965 | A1 | 5/2010 |
| WO | 2011003150 | A1 | 1/2011 |

* cited by examiner

Fig.4
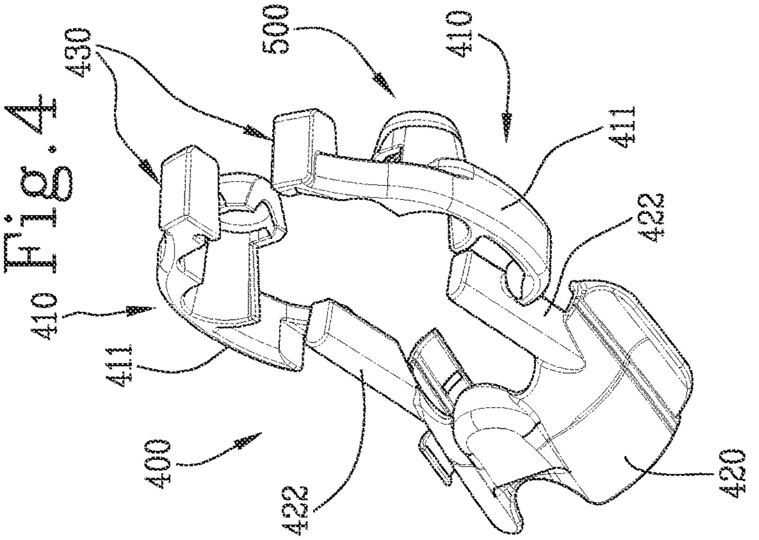
Fig.3
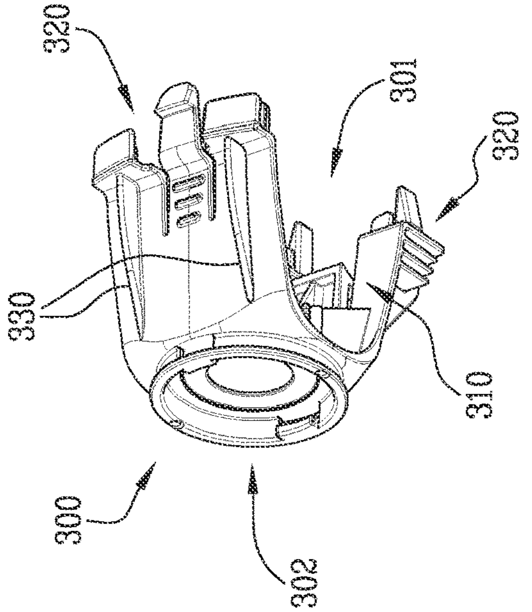
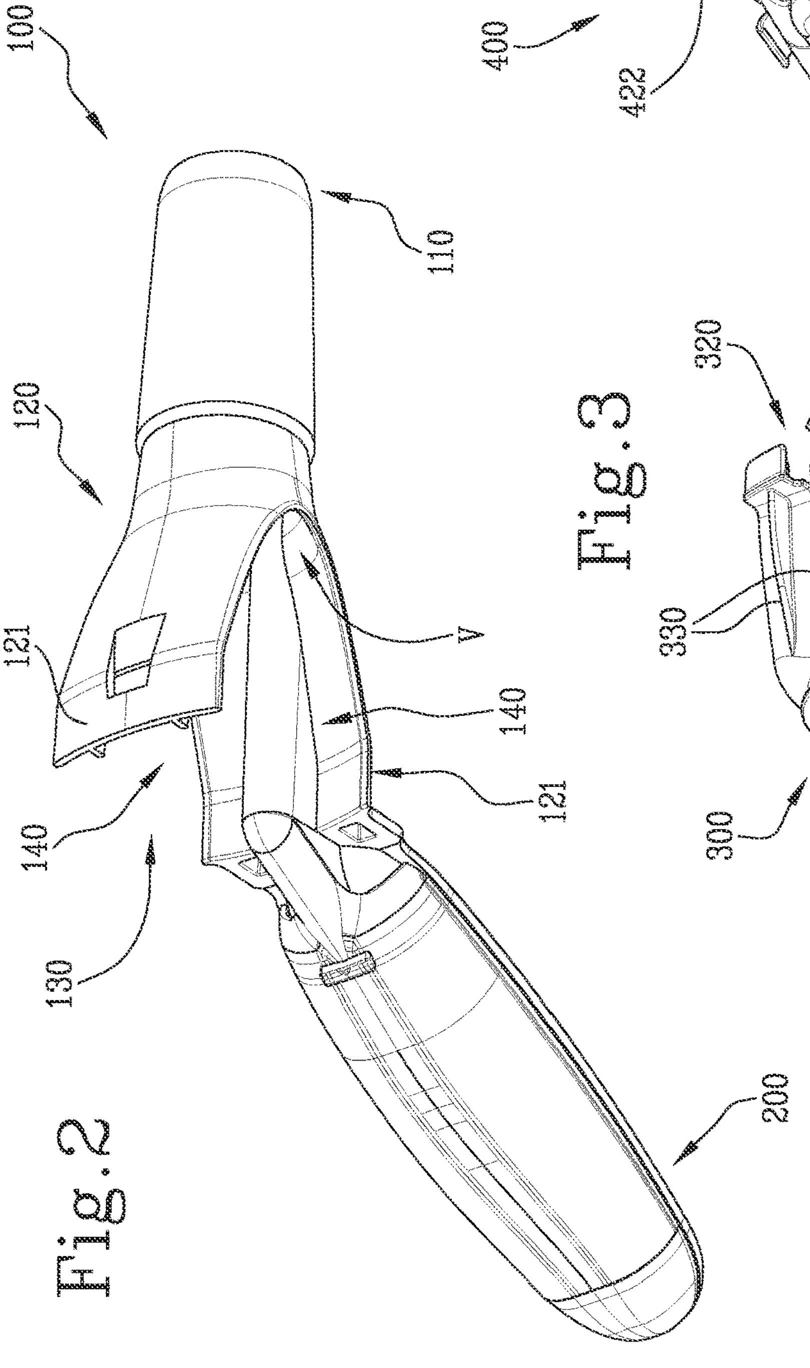
Fig.2

DEVICE FOR INSPECTING A CAVITY OF A PATIENT

The present invention relates to a device for inspecting a cavity of a patient, in particular an internal cavity of a patient, to be understood as a natural cavity, for example anal and/or vaginal cavity, or to be understood as an artificial cavity made by the surgeon.

The following will refer precisely to the field of coloproctology, or to devices such as anoscopes, proctoscopes or rectoscopes, although the present invention may have other diagnostic and/or surgical applications.

As prior art closest to the present invention, the inspection device of the same Applicant described in patent application EP3329834 is considered.

In accordance with this publication, a retractor body which can be coupled to the back of an adapter for a camera is described, and special lateral windows allow the manoeuvring of surgical instruments inside the retractor body to act on the patient's mucosa, while the camera captures the images of the surgery for a convenient display on the monitor. This allows the surgeon an excellent view and high surgical accuracy.

The Applicant has noted that the device described in the above-mentioned patent application, although optimally functional, can be further improved in some respects.

In particular, the lateral windows allow the introduction of surgical instruments but in some cases, for example if lasers are used, the necessary high precision requires a support point for the laser which must otherwise be entirely supported by the surgeon, with difficult exercise of the necessary precision.

Furthermore, supports exist in the prior art which are applied internally to the retractor body to support surgical instruments, however, they are inadequate for the present application as their use would reduce the field of view offered to the camera, thus complicating the surgical procedure. Such supports are usually made by means of special channels which allow the introduction of an elongated instrument, however they preclude a complete movement in the three dimensions, thus hindering more complex surgical manoeuvres.

Therefore, the object of the present invention is to provide a device for inspecting a cavity of a patient which presents high flexibility of use, in particular which allows use with a wide range of surgical instruments including a laser tool.

It is further an object of the invention to provide a device for inspecting a cavity of a patient which allows high operative precision in particular with the use of a laser tool.

The object is substantially achieved by a device for inspecting a cavity of a patient having the features expressed in one or more of the appended claims.

In particular, the inspection device according to the invention comprises a retractor body, extending along a longitudinal axis between a distal end and a proximal end, and a handle applied or fixed to the proximal end of the retractor body to allow an operator to manoeuvre the retractor body according to an insertion and/or rotation movement around the longitudinal axis.

The terms "distal" and "proximal" respectively mean a region farther from the operator (therefore closer to the patient) and closer to the operator in a condition of use of the device.

The retractor body has a distal portion having a substantially tubular and internally hollow shape defining a retraction zone of an internal cavity of a patient. "Tubular" is not meant as a shape with a constant diameter or with an exactly circular section but an internally hollow shape extending around an axis (not necessarily axial-symmetrical), thus defining an internal volume in the form of a longitudinal channel.

The distal portion further has at least one front and/or lateral opening to make a portion of the patient's mucosa or tissue accessible from the internal volume. Such mucosa or tissue can thus protrude within the volume or remain only exposed, as appropriate.

The retractor body also has a proximal portion extending from the distal portion in a diverging fashion, resulting in a rear access opening facing the operator and preferably arranged on the longitudinal axis.

The internal volume of the distal portion is thus accessible from the rear access opening for operating reasons (for the passage of surgical instruments, aspirators or other) or for exploratory reasons (to allow an adequate vision of the surgery zone).

In accordance with an aspect of the invention, the device further comprises at least one support seat arranged in the proximal region of the retractor and configured to supportingly receive a front surface of a laser head. "Support seat" means a generic abutment portion for a front portion of the laser head (or other suitable instrument to be abuttingly retained) to define an at least longitudinal abutment for positioning the laser head.

"Proximal region" means a region of space arranged in a proximal position with respect to the retractor body, however not necessarily coincident with the proximal portion.

Preferably, the support seat is defined by a stop wall having a spherical cap shape having a central opening.

Preferably, the stop wall has the shape of a spherical cap and extends along a closed extension line. Alternatively, the stop wall can also have partially annular extension, i.e., extending along an open line to define an annular section preferably greater than 180° and more preferably greater than 270°. Furthermore, the stop wall defines a central opening for the passage of the laser beam. Such a central opening preferably has a circular shape.

In accordance with an aspect of the invention, the stop wall is defined by a portion of spherical or otherwise concave surface to define a zone intended to partially wrap the front surface of the laser head. Such a configuration allows the front surface of the laser head to be housed with spherical mobility.

Preferably, the support seat also has a conical-shaped (or otherwise converging, flared or of another shape) lateral containment wall and delimiting a receiving volume for the front portion of the laser head. More preferably, such a lateral wall is connected to the stop wall so that the stop wall defines a bottom portion of the receiving compartment. Preferably, in some embodiments, the dimension of the receiving compartment with respect to the dimension of the laser head is determined so as to define a certain degree of rotation for the laser head, in particular of rotation of an amplitude angle comprised between +15° and −20° with respect to the axis of the central opening 520, preferably in the form of a solid angle or "cone". Such a rotation of the laser head is made advantageous by being able to operate on the entire extension of the mucosa visible from the front and/or lateral opening of the distal portion.

In accordance with an aspect of the invention, the support seat is arranged in a radially external position with respect to an external profile of the proximal portion. This has the effect of allowing the adoption of an optimal guide for the laser head without the need to occupy part of the rear view of the device.

That is, the support seat is arranged at a distance from the longitudinal axis which is greater with respect to the greater diameter of the proximal portion. Still in other words, the radial seat is arranged outside the internal volume of the retractor body (where the internal volume is defined by the space included within the distal and proximal portions).

Alternatively, having taken a radial direction passing through the longitudinal axis and on which the support seat lies, the distance of the support seat from the longitudinal axis is greater than the maximum diameter of the retractor body (therefore of the proximal portion) along the same direction.

In some embodiments, the proximal portion has a lateral window, for example defined by a rear recess which interrupts the rear profile (circular, elliptical or other virtually closed shape) of the proximal portion and extends from the rear edge of the proximal portion towards the distal portion. In such a configuration, the lateral window is arranged at the support seat and/or in a position such as to cross a segment joining the support seat and the front and/or lateral opening of the proximal portion. Thereby, the laser head arranged in the support seat can output the laser beam, directing it on the mucosa facing from the opening of the distal portion without interfering with the wall defining the proximal portion.

Preferably, the support seat is arranged in an angular position, around the longitudinal axis, included in the angular extension of the respective lateral window of the proximal portion.

In accordance with an embodiment, the support seat is arranged in an axially spaced position from the proximal portion in the direction opposite to the distal portion. That is, the support seat is stably defined in a position further back from the proximal portion.

In a different embodiment, the support seat can be arranged around the proximal portion, therefore in a position axially included in the axial extension of the proximal portion.

Preferably, the support seat and in particular the stop wall defines a radial protrusion of the retractor body or of an auxiliary body that can be reversibly coupled to the retractor body. More preferably, such a protrusion is at least partially oriented inwards, i.e., towards the longitudinal axis of the retractor body.

The support seat is stably arranged in the desired position in a removable or immovable manner.

In a first embodiment, the support seat is rigidly connected to the proximal portion, in particular integrally made with the proximal portion or irreversibly fixed thereto.

In a second embodiment, the support seat is made on an auxiliary body which is stably applicable to the proximal portion.

In this second embodiment, the auxiliary body may be directly stably connectable to the proximal portion or be connectable to the proximal portion by means of the interposition of an intermediate body, in particular an adapter body preferably for cameras.

In a third embodiment, the support seat is coupled to the retractor body, directly or indirectly, by means of a hinge coupling which allows the movement of the support seat from an active position, in which the support seat is near the front and/or lateral opening of the proximal portion, to an inactive position, in which the support seat is extraneous, i.e., spaced, from the front and/or lateral opening of the proximal portion to allow the surgeon to insert further surgical tools and/or aspiration means to clean the volume inside the retractor body.

In all the cases of removable coupling, the support seat can be applied in a predetermined position, in accordance with a plurality of predetermined positions or in an adjustable manner, in particular continuously in a range of positions.

In an embodiment, the housing seat may be adjustable in the longitudinal direction, parallel to the longitudinal axis of the retractor body.

With reference to the solution with an auxiliary body, it preferably has a pair of arms and a connection portion fixed to the two arms, where at least one of the two arms has a respective support seat. The arms are configured to embrace opposed sides of the proximal portion or the adapter body.

Preferably, but not necessarily, the arms are elastically deformable in approaching and moving away from each other to exercise a "gripper" function. Preferably, the arms each have at least one curved portion defining a concavity and are oriented with the concavities facing each other. More preferably, the support seat is arranged on a respective curved portion.

In an embodiment, the curved portion with the support seat is arranged overlapping the lateral window of the proximal portion. Preferably, the lateral window and the support seat are arranged laterally when the handle is facing downwards.

Preferably, in the case of an auxiliary body applicable to the adapter body, the curved portion with the support seat is arranged overlapping a lateral window of the adapter body or a lateral window defined partly by the proximal portion and partly by the adapter body.

Preferably, moreover, the auxiliary body can be coupled in longitudinal sliding to the adapter body (or to the proximal portion) by one or more linear guides. Preferably, the linear guides are arranged on opposite zones of the curved portions. Thereby, not only is an effective sliding guide of the auxiliary body obtained, but a high shape stability of the curved portions is ensured by virtue of the simultaneous action of the linear guides and the flexural rigidity of the curved portions.

Alternatively, each curved portion has a linear guide arranged at its free end (in particular arranged in a position opposite to the handle of the retractor body) and, at its opposite end, a shape coupling with a portion of the adapter body or of the proximal portion. Thereby, a high shape stability of the curved portions is obtained.

Preferably, the connection portion of the auxiliary body defines a grasping and pushing portion during the assembly and disassembly of the auxiliary body. Preferably, the auxiliary body is configured for a snap connection on the proximal portion or on the adapter body.

Preferably, the adapter body has a first front end provided with a means for reversibly connecting to the retractor body, in particular to the proximal portion, and a second rear end opposite to the first and preferably provided with a means for connecting to an operating accessory, in particular to a camera. In such a solution, the auxiliary body is configured for the application by axial sliding (parallel to the longitudinal axis) on the second end of the adapter body up to an application position arranged in an intermediate position between the first and the second end, preferably with snap or friction locking (with stop abutment) at one or more possible predetermined positions. More preferably, the adapter body has a tapered shape in the direction of the second end, so as to facilitate the assembly of the auxiliary body. Such a tapered shape can only affect the end portion of the adapter body facing the second end.

More generally, in the solution in which the support seat is defined on the adapter body directly (integral with the adapter body or fixed thereto) or indirectly (by application of the auxiliary body), the support seat can be arranged outside the adapter body, i.e., in a radially external position with respect to the external profile of the adapter body, or inside the adapter body, i.e., in a radially external position with respect to the external profile of the adapter body, or straddling a lateral window obtained on the adapter body, i.e., at the external profile of the adapter body.

It is further possible that the auxiliary body has the support seat in a position facing inwards so that, once the auxiliary body is applied on the adapter body, the support seat is arranged at the external profile of the adapter body or internally with respect to the external profile of the adapter body.

In accordance with a further aspect of the invention, the central opening of the support seat has an axis a (of axial symmetry), defined by joining the centre of the central opening 520 and the centre of the support seat 500 in the shape of a spherical dome, inclined by an acute angle with respect to the longitudinal axis of the retractor body. Such an acute angle is preferably comprised between 0° and 30°, more preferably between 5° and 20°.

In accordance with a preferred solution of the invention, the device has two support seats arranged on opposite sides with respect to the longitudinal axis, in particular in symmetrical positions with respect to a longitudinal plane of symmetry of the retractor body.

Likewise, in such a configuration the retractor body and/or the adapter body (where included) have respective lateral windows. Furthermore, the auxiliary body, if any, has a support seat on each side, in particular one on each arm.

In this embodiment, the support seats are arranged so that the respective central openings have converging axes. Furthermore, each support seat is preferably oriented so as to have the axis of the central opening at a side opposite the front opening of the distal portion or the lateral opening opposite to the distal portion.

With reference to the laser head, it is configured for the emission of a laser beam and has a means for connecting to an electrical or laser source. In accordance with an aspect of the invention, the laser head comprises a spherical front surface engageable in a support relationship with said support seat. Such a spherical front surface can be defined by a convex surface defining a hemisphere, a sphere portion greater than a hemisphere or a sphere portion less than a hemisphere. Preferably, moreover, the radius of curvature of the spherical surface of the laser head is substantially identical to the radius of curvature of the stop wall. Thereby, a perfect spherical coupling between the laser head and the support seat is generated.

A preferred, but not exclusive, embodiment of a device for inspecting a cavity of a patient in accordance with the present invention is now illustrated by way of non-limiting example.

With reference to the appended figures:

FIG. 2 shows in axonometric view a first component of the device of FIG. 1;

Figure 1:
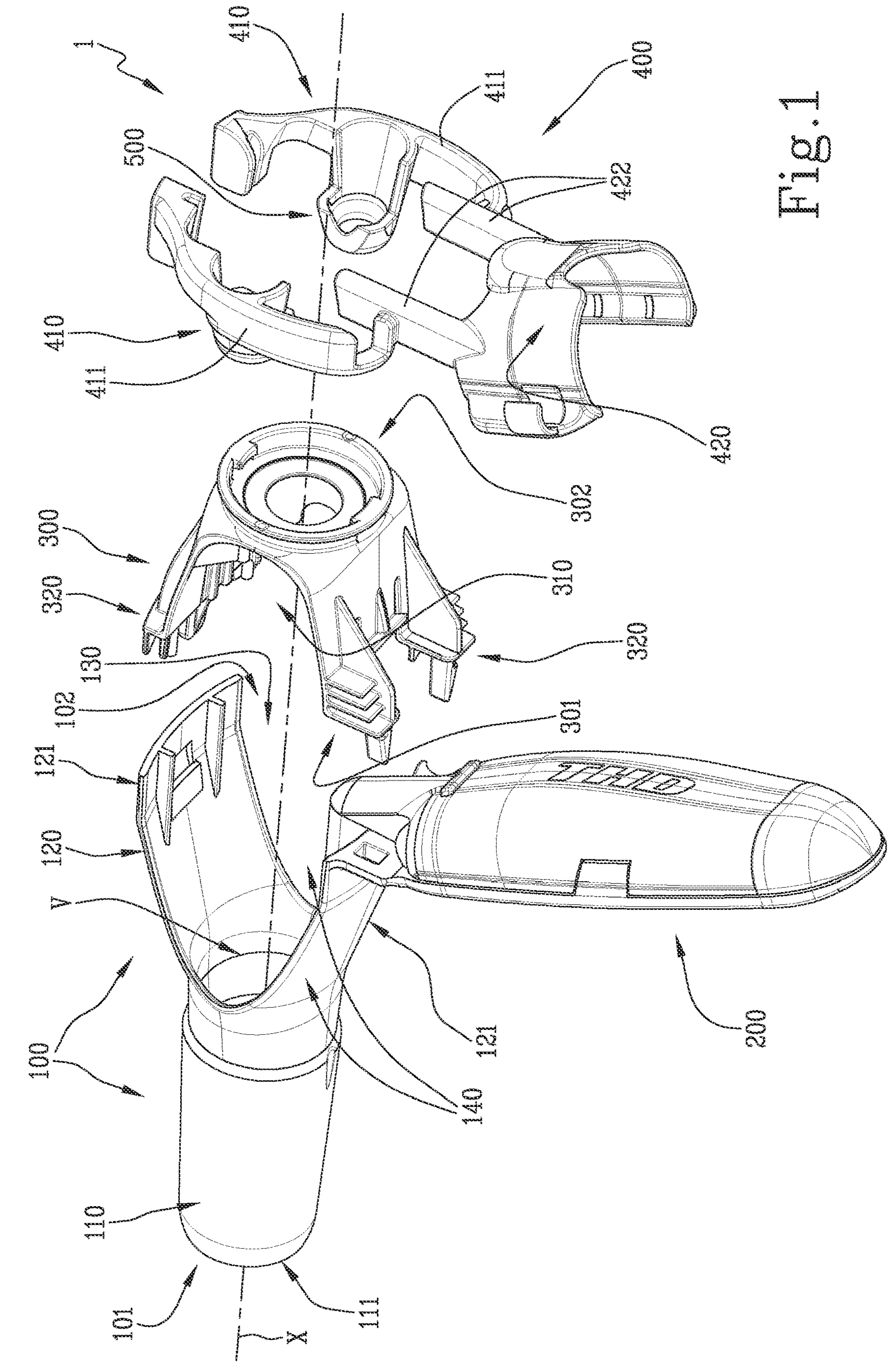
FIG. 1 shows an exploded view of a device for inspecting a cavity of a patient in accordance with the present invention.
Figure 6:
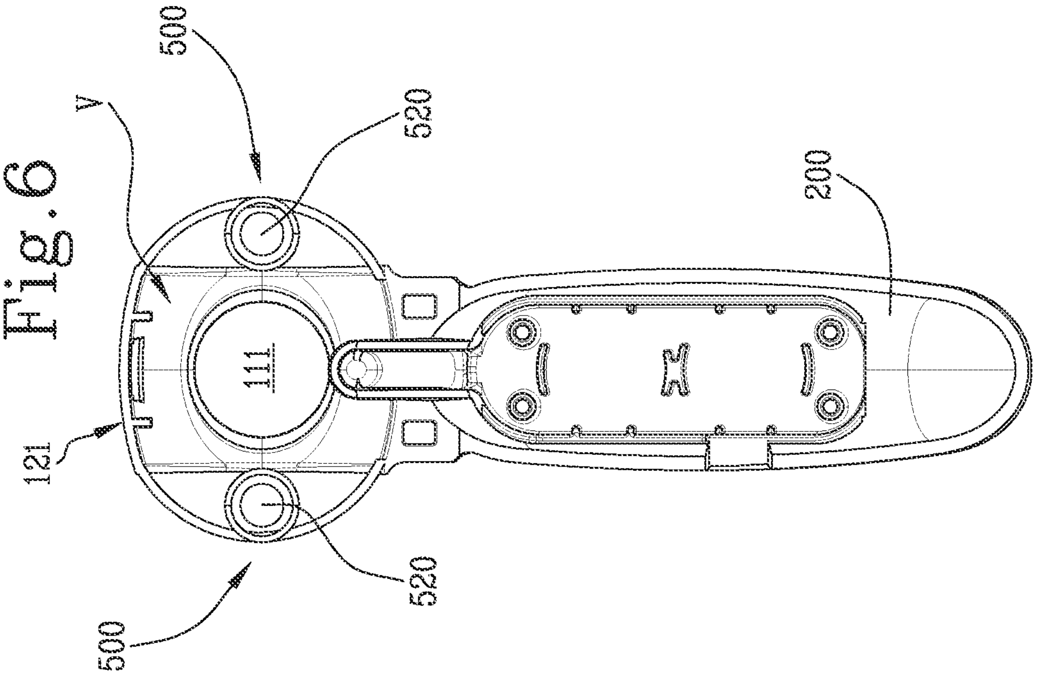
Figure 5:
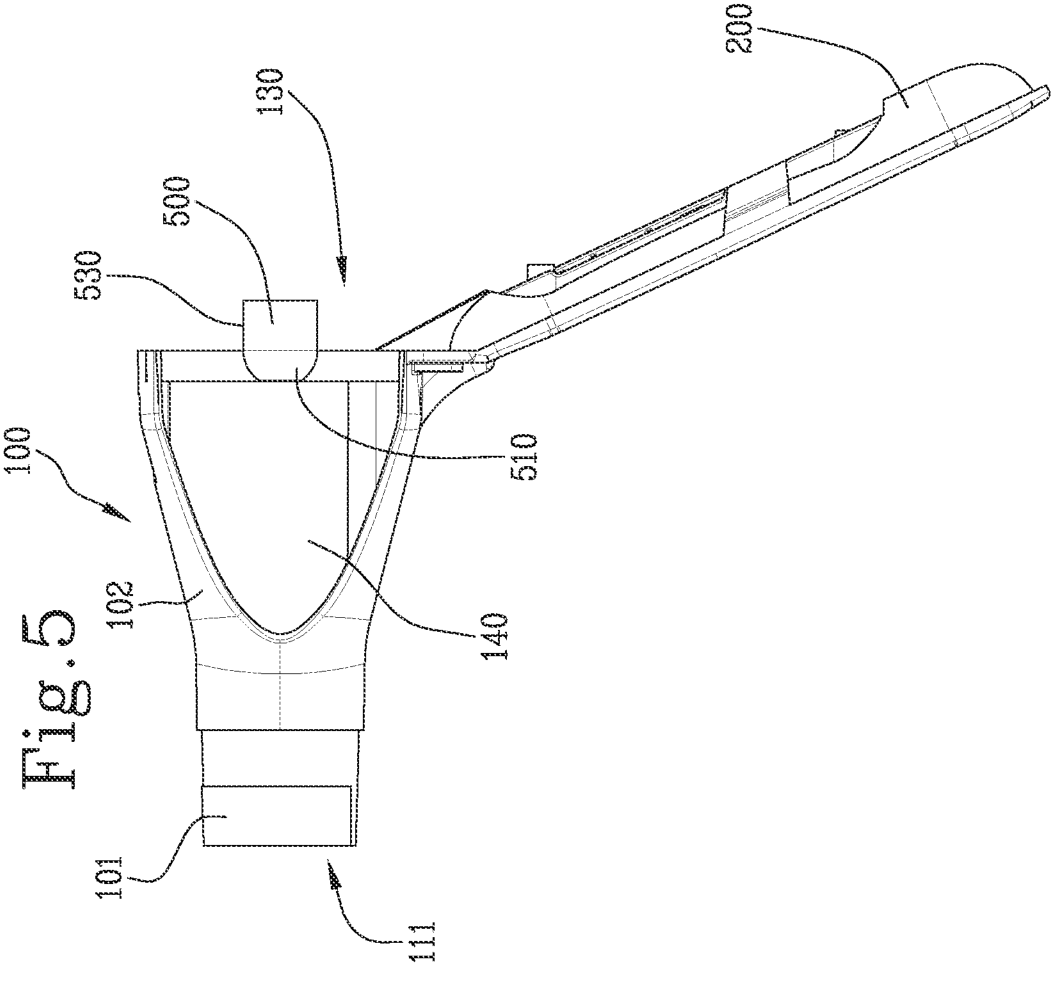
Figure 8:
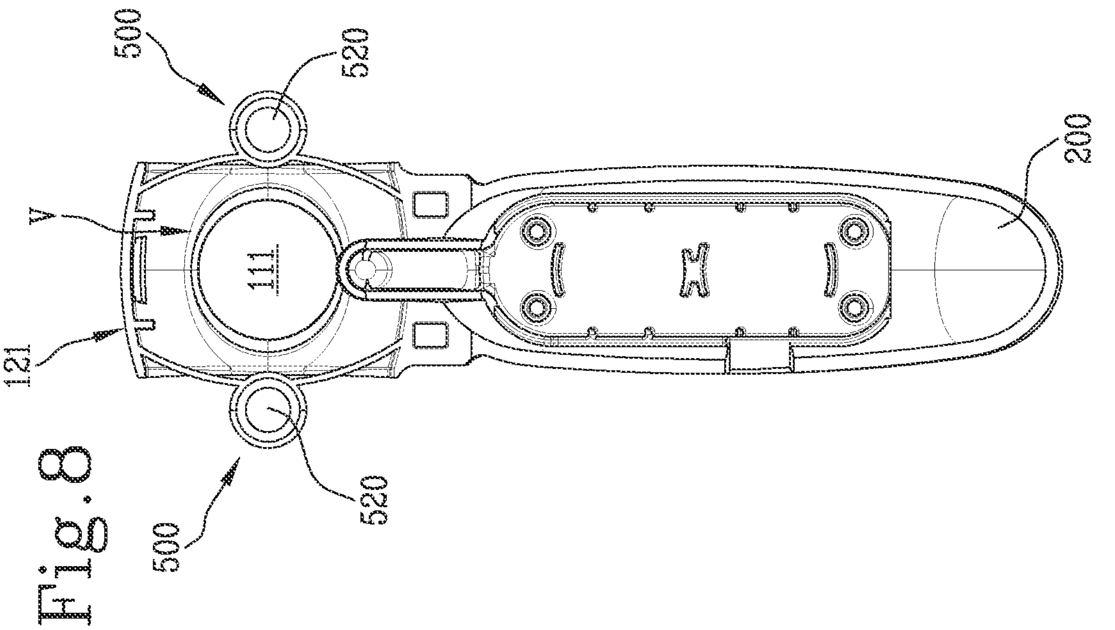
Figure 7:
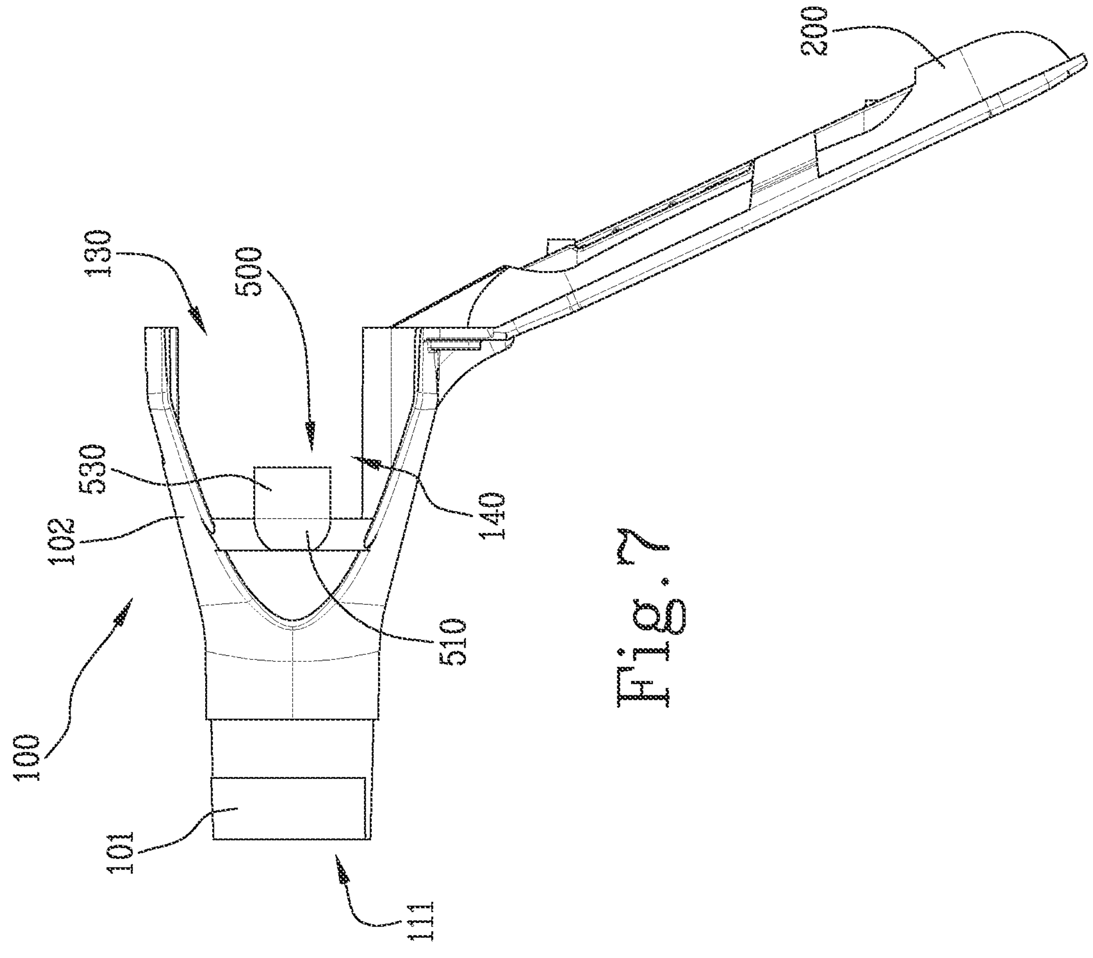
Figure 10:
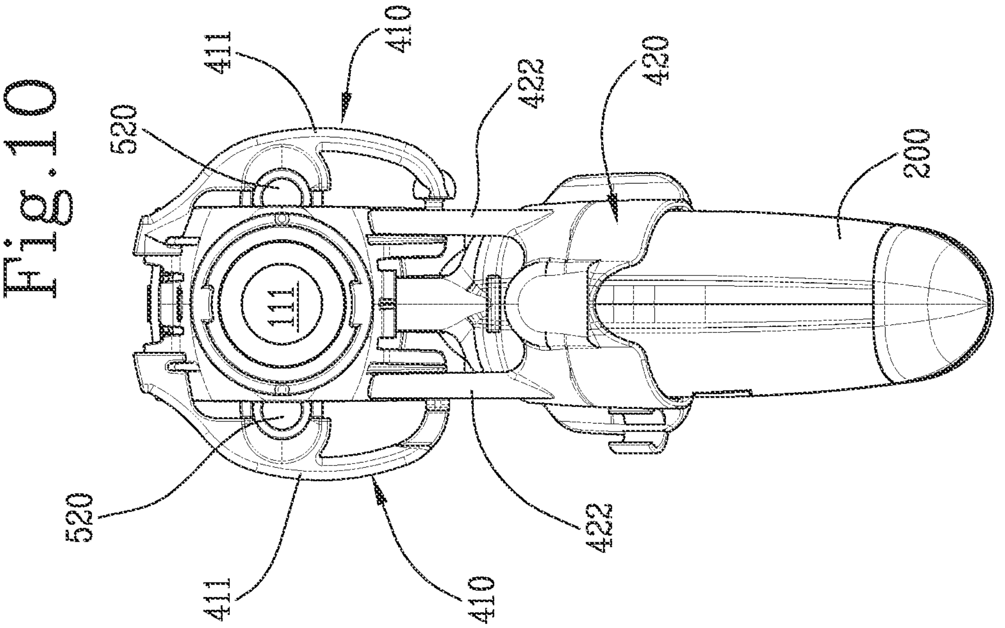
Figure 9:
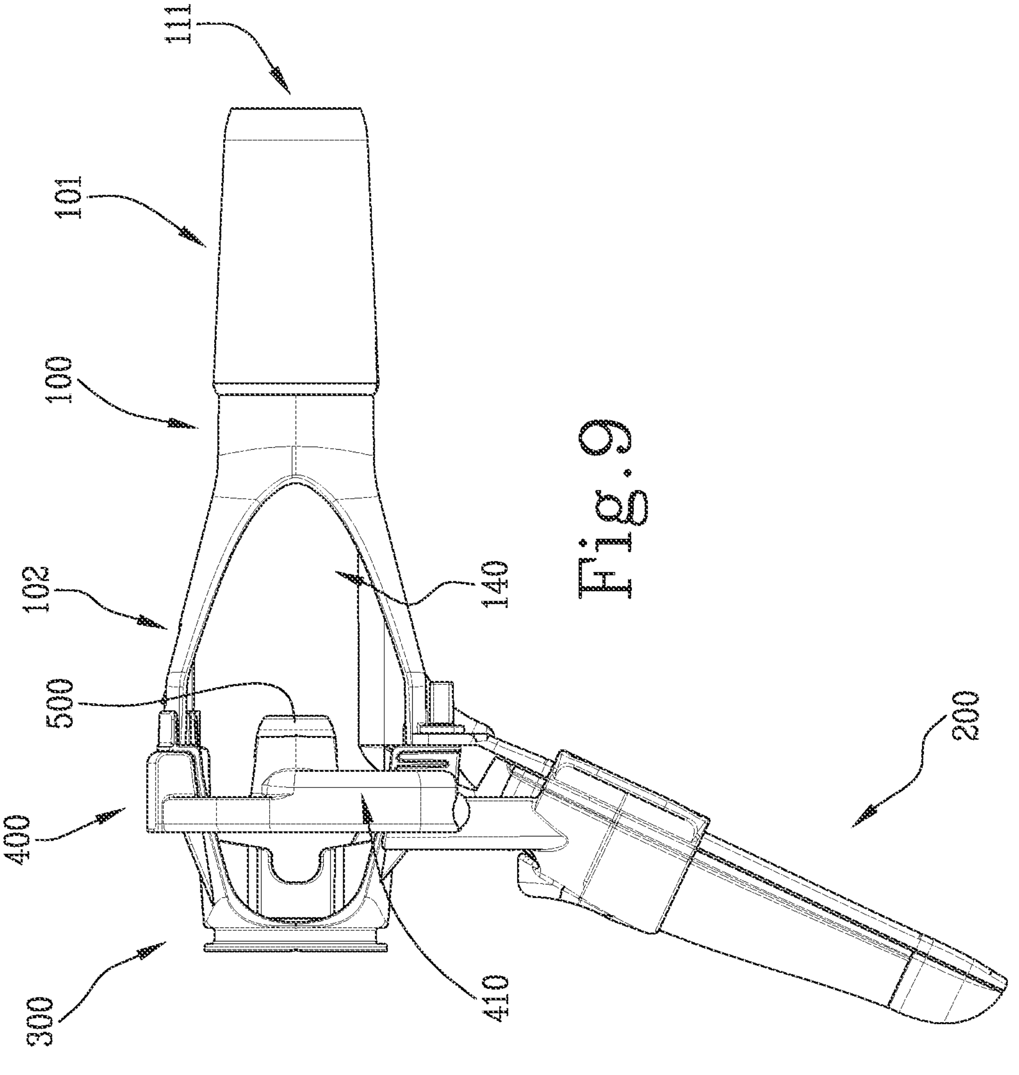

FIGS. 3 and 4 respectively show in axonometric view a second and a third component of the device of FIG. 1;

FIGS. 5 and 6 show in side view and in front view, respectively, a first variant of the first component of FIG. 2;

FIGS. 7 and 8 show in side view and in front view, respectively, a second variant of the first component of FIG. 2;

FIGS. 9 and 10 illustrate in side view and in front view, respectively, the device of FIG. 1 in an assembled configuration.

Figure 12:
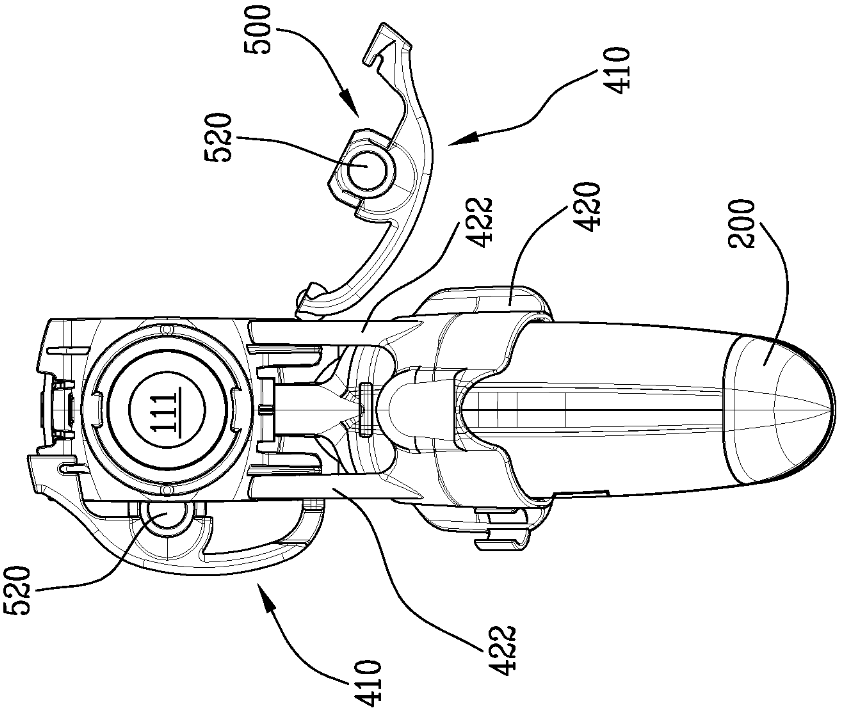
Figure 11:
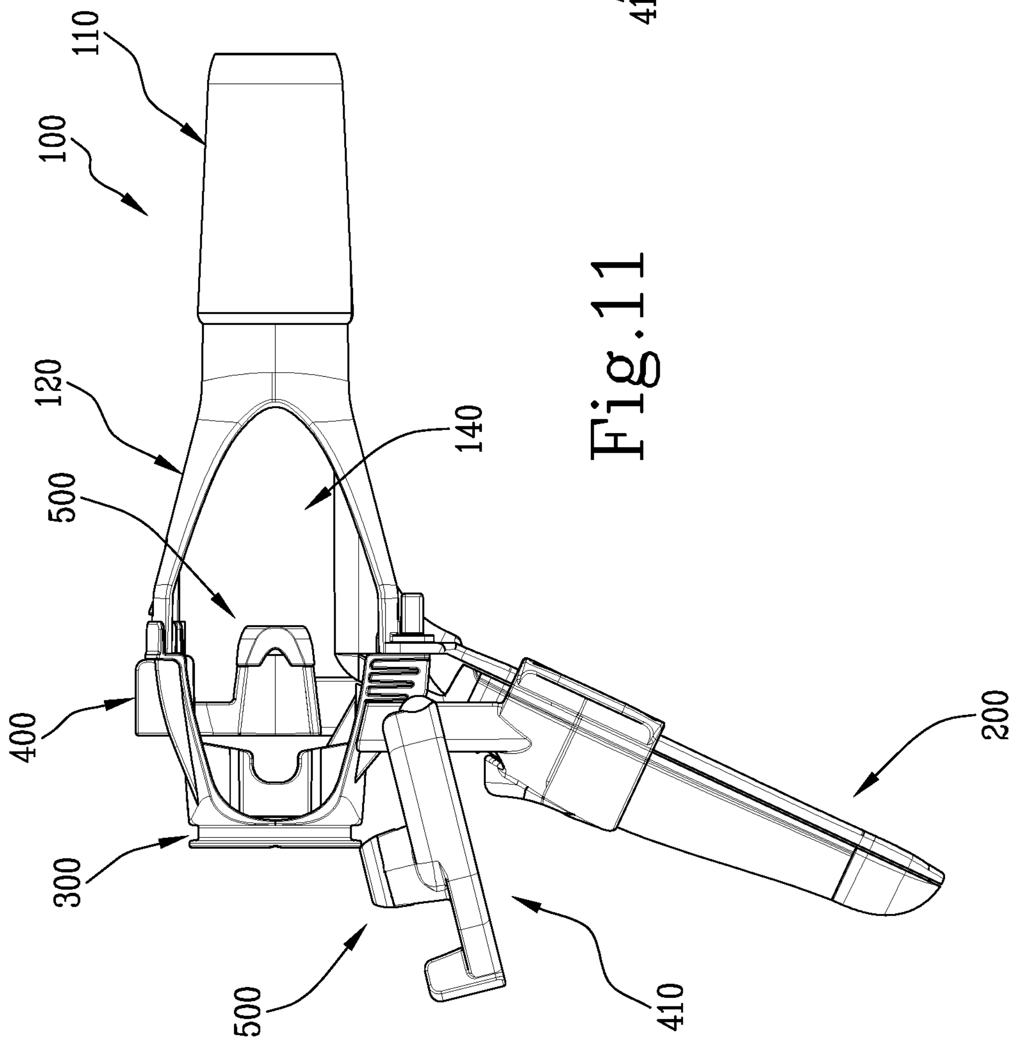
Figure 13:
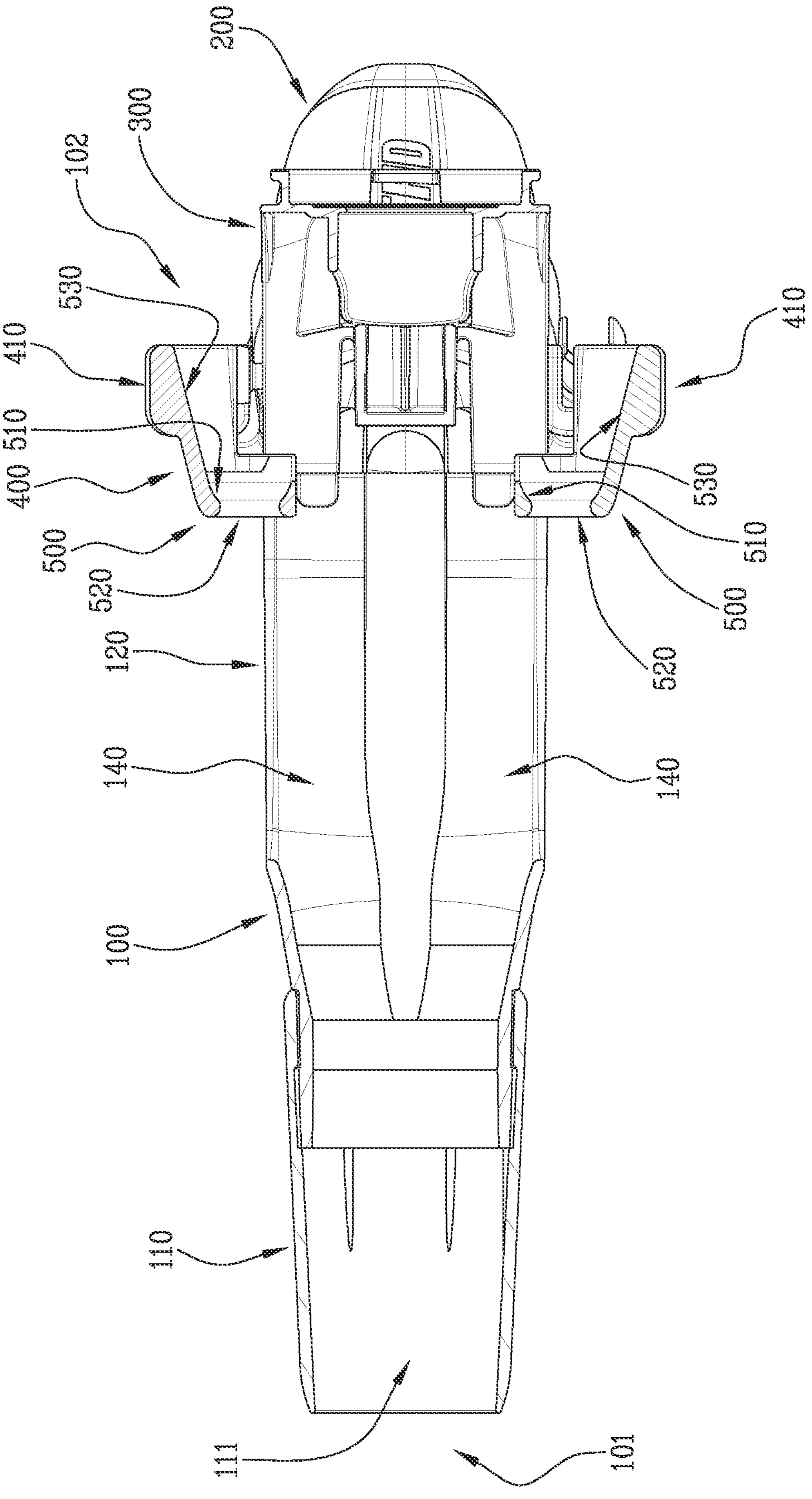
Figure 14:
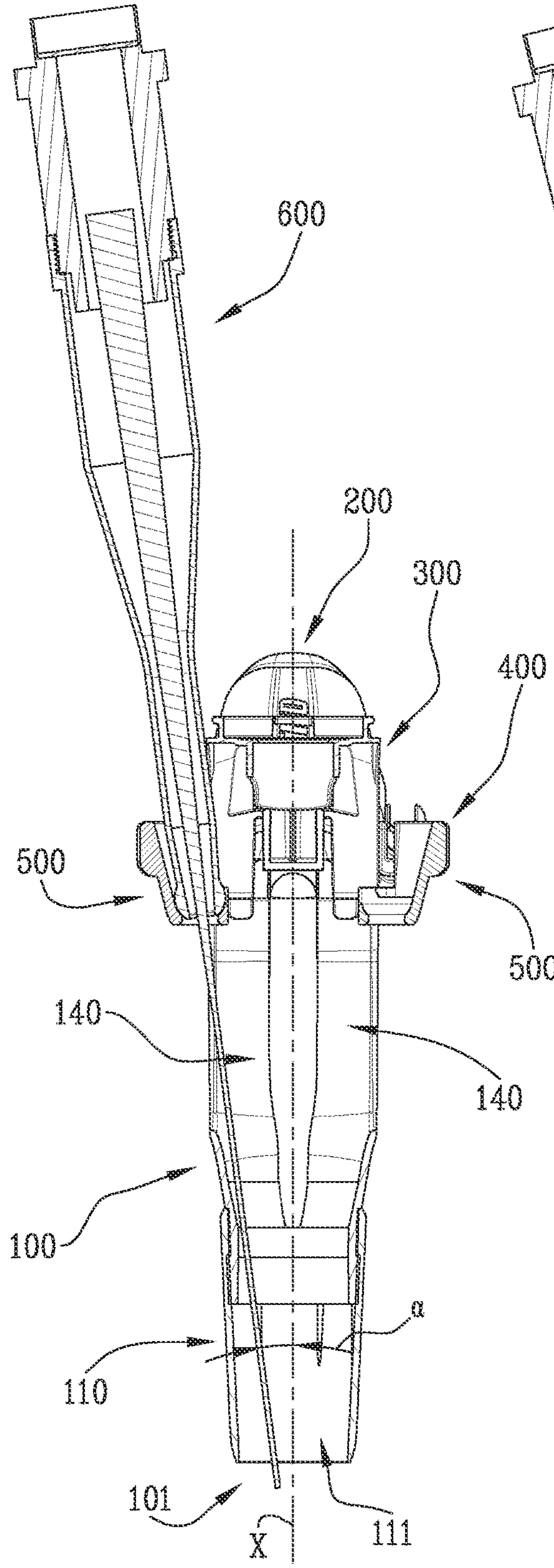
Figure 15:
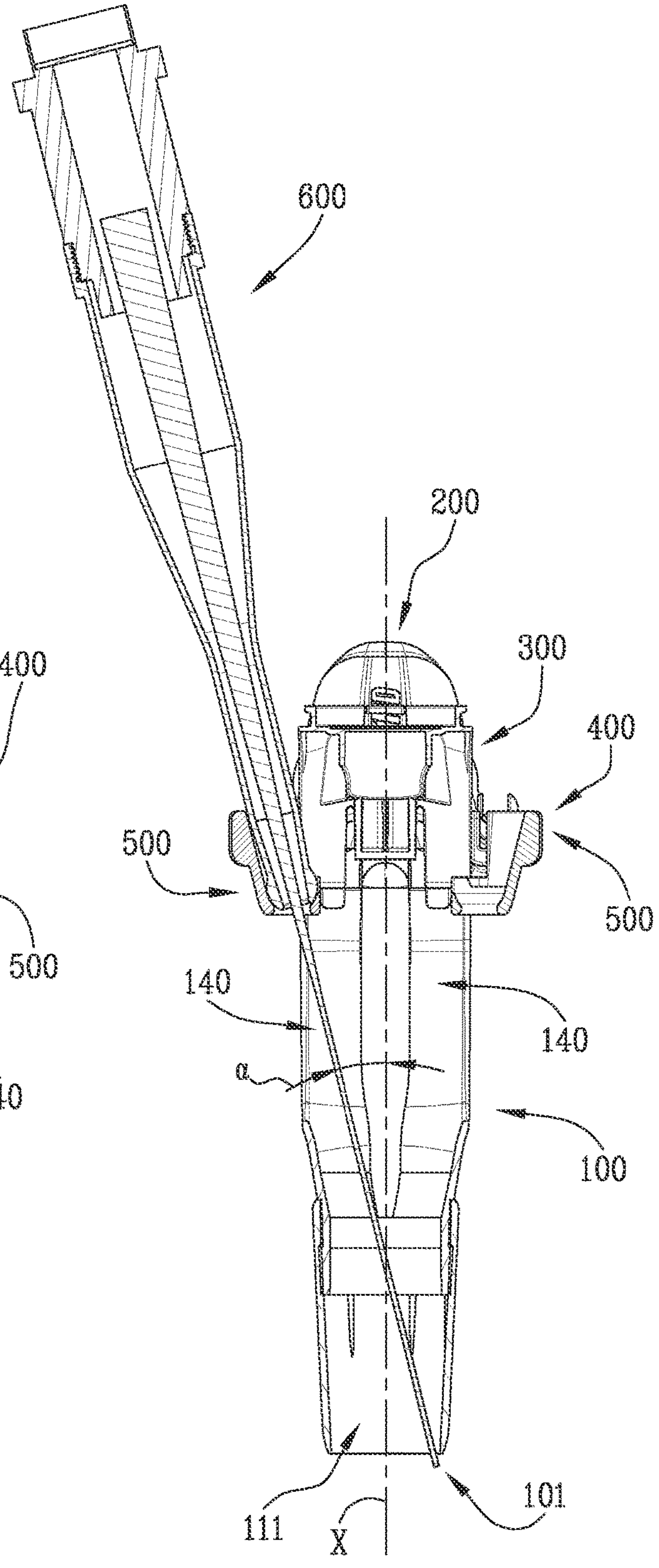
Figure 16:
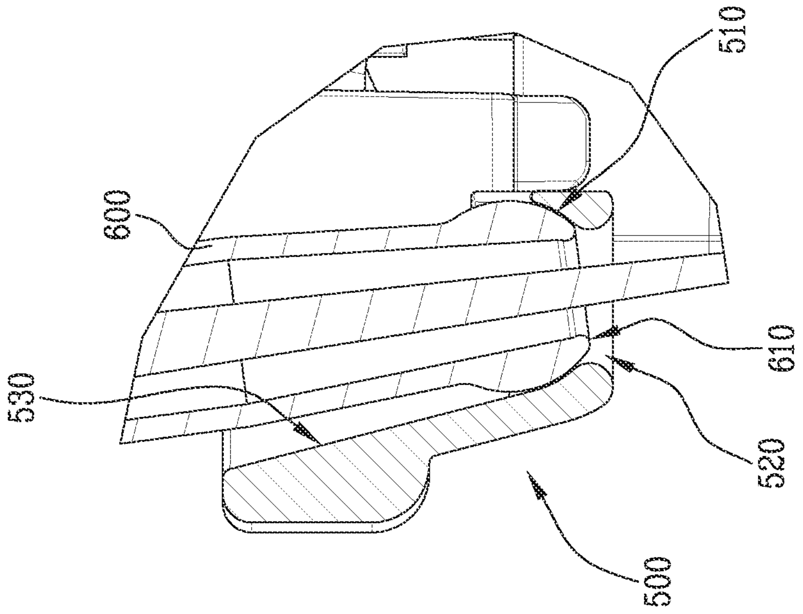

FIGS. 11 and 12 illustrate in side view and in front view, respectively, a second embodiment of the device of FIG. 1, illustrated in an assembled configuration, in which a component is shown in an operative arrangement;

FIG. 13 illustrates, in longitudinal section, a top view of the device of FIG. 1 in the assembled configuration;

FIGS. 14 and 15 illustrate in longitudinal section seen from above the device of FIG. 1 in a use relationship with a fourth component;

FIG. 16 illustrates in enlarged section the fourth component in a use relationship with an enlarged portion of the device of FIG. 1.

Figure 17:
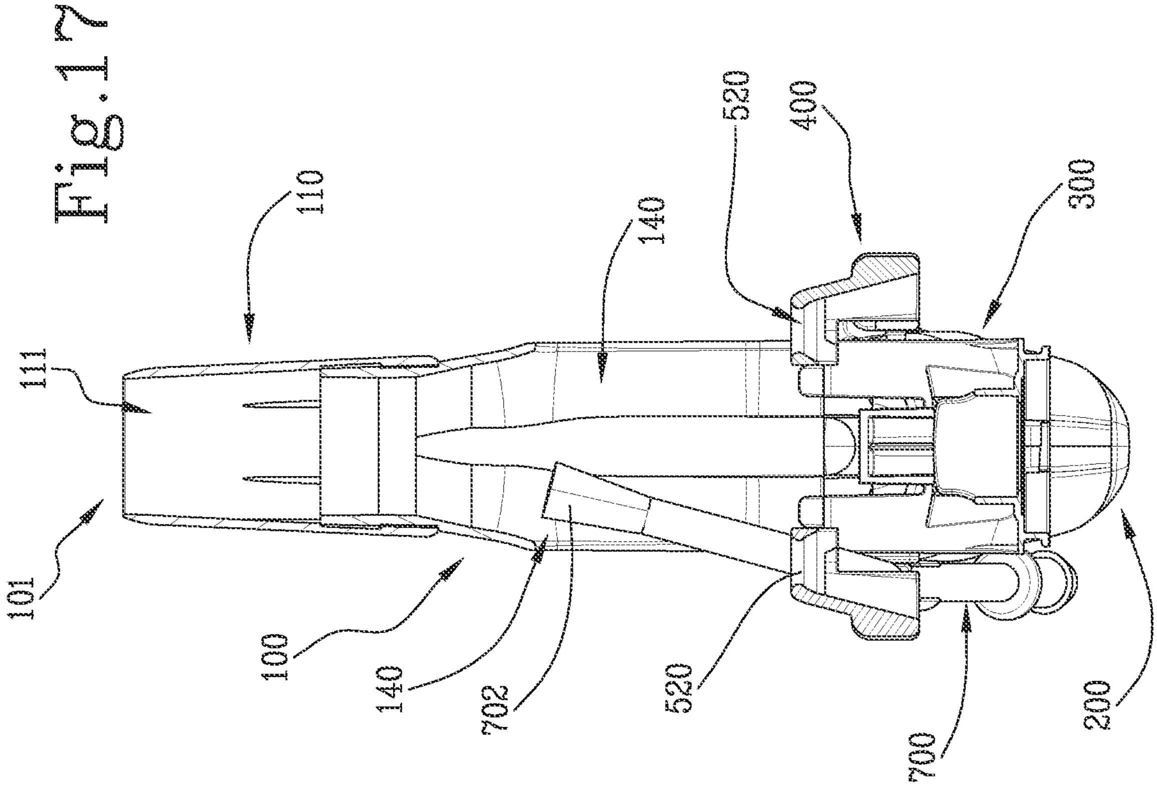
Figure 18:
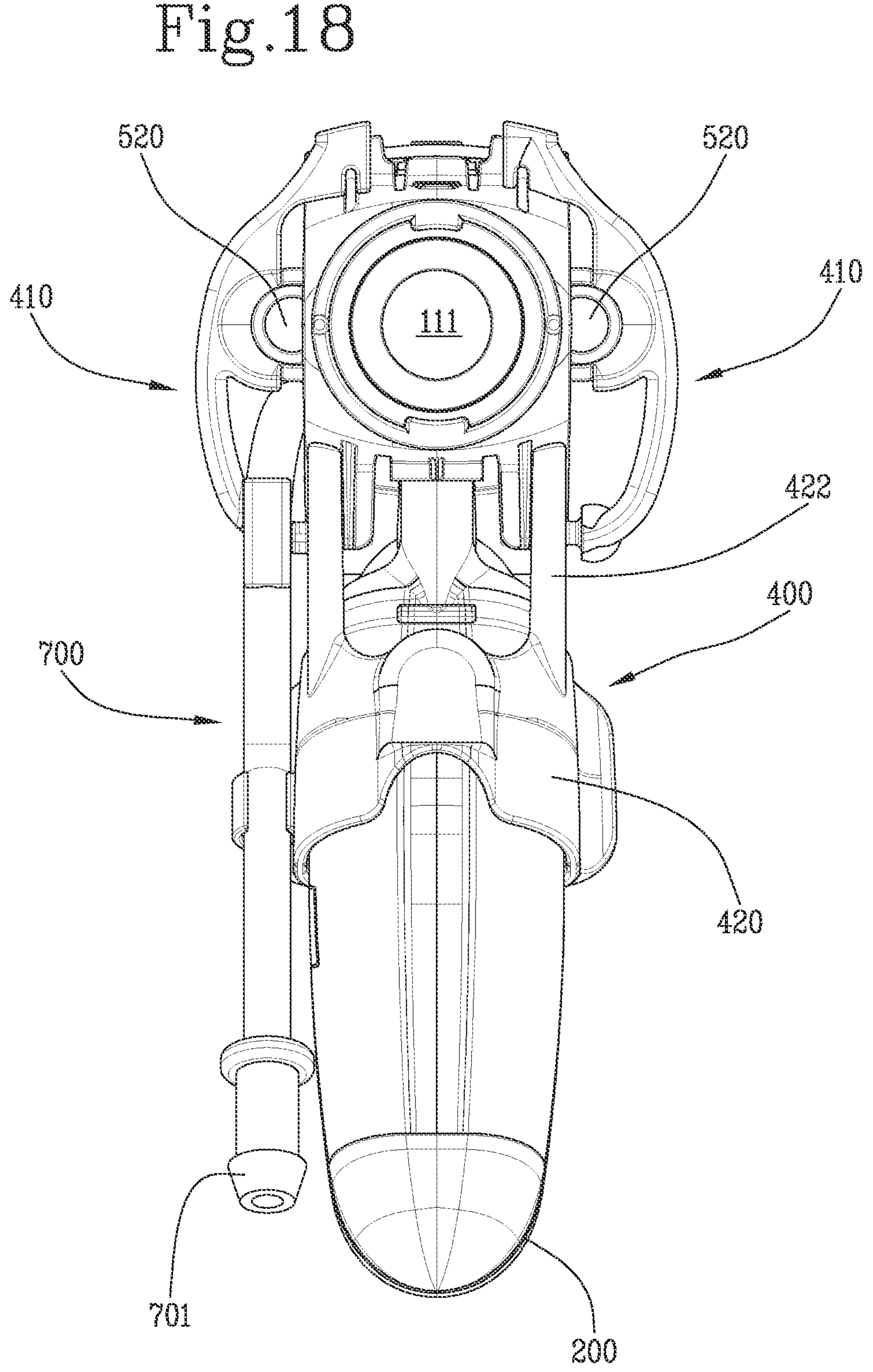

FIGS. 17 and 18 illustrate in longitudinal section seen from above and in front view, respectively, the device of FIG. 1 with a fifth component.

In accordance with the appended figures, an inspection device in accordance with the invention is indicated overall by 1.

In the illustrated embodiment, the device 1 comprises a retractor body 100, a handle 200, an adapter body 300 and an auxiliary body 400. Preferably, the three bodies and the handle 100, 200, 300, 400 are made of plastic material, more preferably transparent or semi-transparent.

The retractor body 100 extends along a longitudinal axis "X" between a distal end 101 and a proximal end 102 and has a distal portion 110 and a proximal portion 120. The distal portion 110 has a substantially tubular and internally hollow shape defining a retraction zone of an internal cavity of a patient.

The definition "tubular" does not exclude the possibility that the external shape of the distal portion 110 has a slightly tapered shape or is provided with a section which is not perfectly circular (it could also be elliptical, oval or still other), since the specific shape of the distal portion 110 can be selected as a function of needs without departing from the same inventive concept of the invention.

The distal portion 110 thus extends along the longitudinal axis "X" and defines an internal volume "V" in the form of a longitudinal channel.

The distal portion 110 further has at least one anterior or front end 111 to make a portion of the patient's mucosa or tissue accessible from the internal volume "V". Such mucosa or tissue can thus protrude within the volume or remain only exposed, as appropriate. The front opening 111 could be replaced by a pair of opposed lateral openings, in accordance with an embodiment not illustrated, in which the lateral openings are arranged in the front region of the distal portion 110. Alternatively, the front opening 111 could itself extend on the sides up to extending to the lateral wall of the distal portion 110.

The proximal portion 120 extends from the rear edge of the distal portion 110 in a diverging fashion and opens in a rear access opening 130 facing the operator and arranged on the longitudinal axis "X". Such a rear access opening 130 thus allows visual and instrumental access to the internal volume "V" and, therefore, to the mucosa accessible through the front and/or lateral opening 111 of the distal portion 110.

In the illustrated embodiment, the proximal portion 120 has two opposed lateral windows 140 which preferably extend substantially along the entire axial extension of the proximal portion 120, thus from the rear edge of the proximal portion 120 to the distal portion 110. They could, however, be less extensive or alternatively more extensive, in the latter case also affecting part of the distal portion 110. Such lateral windows 140 define further zones of visual and instrumental access to the internal volume "V".

The lateral windows 140 are preferably defined by respective rear recesses which interrupt the profile of the rear edge of the proximal portion 120 and thus extend from the rear edge of the proximal portion 120 towards the distal portion 110.

In the illustrated embodiment, therefore, the proximal portion 120 is substantially defined by two opposed lobes 121, one upper and one lower connected to each other with a desired radius of curvature at the junction zone between the proximal portion 120 and the distal portion 110.

The handle 200 is applied to the proximal portion 120, in a lower region of the retractor body 100 and in particular to one of the aforementioned lobes 121. Such a connection between the proximal portion 120 and the handle 200 can be made integrally or with stable reversible or irreversible application.

The handle 200 allows the operator to manoeuvre the retractor body 100 according to an insertion and/or rotation movement around the longitudinal axis "X". In use, the handle 200 is normally oriented downwards and, although it may take different orientations in use, in the context of the present invention the definition of "low" and "high" are to be understood as "in the extension region of the handle 200" and "in the direction opposite the handle 200". Similarly, the definition of "lateral" applies, referring to the handle 200 normally facing downwards.

The adapter body 300 is stably reversibly applicable to the retractor body 100, in particular to the proximal portion 120 and more in particular to the two lobes 121.

The coupling of the adapter body 300 is operable in a known manner, for example with snap systems, and thus will not be described in detail.

The adapter body 300 has a first front end 301 provided with a means for reversibly connecting to the retractor body 100, in particular to the proximal portion 120, and a second rear end 302, opposite to the first and preferably provided with a means for connecting (known, for example snap or with screws) to an operating accessory, in particular to a camera "T".

Preferably, the adapter body 300 has a tapered shape in the direction of the second end 302, where such a tapered shape can only affect the end portion of the adapter body 300 facing the second end 302.

Preferably, the adapter body 300 also has a pair of opposed lateral windows 310, intended in use (i.e., after the connection with the retractor body 100) to join with the aforementioned lateral windows 140 of the proximal portion 120. That is, each lateral window 140 of the retractor body 100 is intended to face a corresponding lateral window 310 of the adapter body 300, thus defining the extension of the other and, therefore, a single lateral window of preferably elliptical shape or in any case elongated along the longitudinal axis "X".

To this end, the lateral windows 310 of the adapter body 300 also extend from the front edge of the adapter body 300, defining the first end 301, up to an intermediate area of the adapter body 300. Therefore, such lateral windows 310 are also preferably defined by respective front recesses which interrupt the profile of the front edge of the adapter body 300.

That is, therefore, the adapter body 300 can also have a pair of opposed lobes 320, upper and lower, arranged frontally at the first end 301 and each removably connectable to a respective lobe 121 of the retractor body 100.

The auxiliary body 400 is stably and removably applicable to the retractor body 300, in particular by application to the external surface of the adapter body 300, more in particular to an axially central portion of the adapter body 300.

The auxiliary body 400 is configured for the application by axial sliding (parallel to the longitudinal axis "X") on the second end of the adapter body up to an application position arranged in an intermediate position between the first and the second end 301, 302, preferably with snap or friction locking (with stop abutment) at one or more possible predetermined positions.

From the structural point of view, the auxiliary body 400 has a pair of mutually adjacent arms 410 and a connection portion 420 fixed below the two arms 410 to keep the arms 410 in position. The arms 410 are configured to embrace opposed sides of the adapter body 300.

The arms 410 each have at least one curved portion 411 defining a concavity and are oriented with the concavities facing each other. In the illustrated embodiment, the curved portion 411 is arranged at the free end of the arm 410 while the other end of the arm 410 is connected to the connection portion 420 and is preferably defined by a straight portion 422.

Preferably, but not necessarily, the arms 410 are elastically deformable approaching and moving away from each other to exert a "gripping" function on the external surface of the adapter body 300.

In the illustrated embodiment, the curved portion 411 is arranged overlapping the respective lateral window 140, 310, in particular the respective lateral window 310 of the adapter body 300.

At least one of the arms 410, preferably each of them, supports or defines a support seat 500, in particular arranged on the curved portion 411. Therefore, the support seat 500 is also arranged overlapping the respective lateral window 310 of the adapter body 300, and in particular in a radially external position with respect to said lateral window 310.

The support seat 500 is configured to supportingly receive a front surface 610 of a laser head 600. "Support seat" means a generic abutment portion for a front portion of the laser head (or other suitable instrument to be abuttingly retained) to define an at least longitudinal abutment for positioning the laser head. To this end, the support seat 500 is arranged at least in part transversely to the longitudinal axis "X".

In more detail, the support seat 500 is defined by a stop wall 510 having a spherical cap shape, thus with closed extension, having a central opening 520. The central opening 520 is intended for the passage of the laser beam and is preferably circular.

The stop wall 510 is defined by a portion of spherical or otherwise concave surface to define a zone intended to partially wrap the front surface 610 of the laser head 600. Such a configuration allows the laser head 610 to be housed with spherical mobility in the support seat 500.

Preferably, the support seat 500 also has a conical-shaped (or otherwise converging, flared or of another shape) lateral containment wall 530 and delimiting a receiving volume for the front portion of the laser head 600. More preferably, such a lateral containment wall 530 is connected to the stop wall 510, in particular continuously, so that the stop wall 510 defines a bottom portion of the receiving compartment. The dimension of the receiving compartment with respect to the dimension of the laser head 600 is determined so as to define a certain degree of rotation for the laser head 600, in particular of rotation of an amplitude angle comprised between +15° and −20° with respect to the axis of the central opening 520, preferably in the form of a solid angle or "cone".

Preferably, the auxiliary body 400 can be coupled in longitudinal sliding to the adapter body 300 by one or more linear guides 330, 430. Preferably, the linear guides 330, 430 are arranged at least on one end portion of each arm 410 and in a complementary manner on a top portion of the adapter body 300. In such an embodiment, the linear guides can be of the form-coupled relief-groove type. Thereby, not only is an effective sliding guide of the auxiliary body 400 obtained, but a high shape stability of the curved portions 411 and a high positional stability of the support seat 500 is ensured by virtue of the simultaneous action of the linear guides 320, 430 and the flexural rigidity of the curved portions 411.

In an embodiment, illustrated in FIGS. 8 and 9, at least one of the two arms 410 is coupled, directly or indirectly, to the retractor body 100 through a hinge connection and is movable from an operative position, in which the arm 410 is in the raised position and the support seat 500 is near the front opening 111 and/or one of the lateral windows 140, to an inoperative position, in which the arm 410 is in the lowered position and the support seat 500 is extraneous, i.e., spaced, to the front opening 111 and/or one of the lateral windows 410.

In the operative position, the at least one arm 410 is near the front opening 111 and/or a lateral opening 140 and the support seat 500 is usable by the surgeon.

In the inoperative position, the at least one arm 410 is overturned and near the handle 200, placing the support seat 500 in an extraneous position from the retractor body, in particular from the front opening 111 and from the lateral opening 140. In this latter position, the surgeon can have the front opening 111 and/or at least one of the lateral windows 410 free so as to be able to insert further surgical tools including aspiration means 700 adapted to aspirate blood, smoke, and small fragments of mucous tissue, freeing the internal volume V of the retractor body 100.

Preferably, each curved portion also has at its own portion or end opposite the linear guide 430, a shape coupling 440 with a corresponding portion of the adapter body 300, in particular an elbow curvature such as to embrace a corresponding lateral or lower convex portion of the adapter body 300. Thereby, a high shape stability of the curved portions 411 is again obtained. Preferably, the connection portion 420 of the auxiliary body 400 defines an axial grasping and pushing portion during the assembly and disassembly of the auxiliary body 400, where such sliding is initially facilitated by the tapered shape of the rear area of the adapter body 300.

Preferably, moreover, the connection portion 420 has a concave shape and/or is substantially counter-shaped to a corresponding portion of the handle 200 to which it is abutted in an assembly configuration of the auxiliary body 400.

In the illustrated embodiment, the support seats 500 are arranged on the respective arms 410 so as to result, following the application of the auxiliary body 400 on the adapter body 300, in a radially external position with respect to the window 310, i.e., outside the external profile of the adapter body 300.

However, non-illustrated embodiments are possible in which the support seats 500 are arranged on the respective arms 410 so as to result, following the application of the auxiliary body 400 on the adapter body 300, in a radially internal position to the windows 310 or straddling the windows 310 themselves.

Preferably, the central opening 520 of the support seat 500 has an axis (of axial symmetry) inclined by an acute angle with respect to the longitudinal axis "X" of the retractor body 100. Such an acute angle is preferably comprised between 0° and 30°, more preferably between 5° and 20°.

Preferably, the support seat 500 has a conical-shape lateral containment wall 530 defining a pair of generatrices passing through the centre of the stop wall 510 in the shape of a spherical cap. Thereby, the laser head 600 arranged in a support seat 500 can direct a laser beam exclusively in the direction of the front or lateral opening 111 of the distal portion 110 and in particular in an area thereof arranged on the opposite side with respect to the support seat 500. That is, the support seats 500 are inclined so as to convergingly direct the axes of the respective central openings 520.

With reference to the laser head 600, it is configured for the emission of a laser beam and has a means for connecting 620 to an electrical or laser source. The front surface 610 of the laser head 600 has a spherical shape engageable in a support relationship with each support seat 500. Such a spherical front surface 620 can be defined by a convex surface defining a hemisphere, a sphere portion greater than a hemisphere or a sphere portion less than a hemisphere. Preferably, moreover, the radius of curvature of the spherical surface of the laser head 600 is substantially identical to the radius of curvature of the stop wall 510. Thereby, a perfect spherical coupling between the laser head 600 and the support seat 500 is generated.

In use, once the retractor body 100 is inserted in position in the cavity of the patient, the operator can intervene on the mucosa by means of surgical instruments through the lateral windows 140, 310 and/or proceed with a laser operation by arranging the laser head 600 in rotational support inside one of the support seats 500 and rotating the laser head 600 if necessary to move the laser beam, directing it to the desired region of the mucosa. Furthermore, in case of need, the operator can remove the laser head 600 from the support seat 500 and arrange it in the other support seat 500 so as to operate on another mucosa portion which is adjacent to or distinct from the one on which he previously intervened.

As can be seen in the appended FIGS. 20 and 21, the device 1 further comprises an aspiration means 700, removably connected to the handle 200 and having a first termination 701, placed in adherence to the handle 200 and connected to a vacuum source (not illustrated in the appended figures), and a second termination 702, opening in the volume V underlying the retractor body 100. The aspiration means 700 is preferably defined by a tubular body, placed in vacuum by the vacuum source, to aspirate, inside the volume V, any smoke produced by the use of the laser 600. In particular, the second termination 700 ends with a duckbill portion, located inside the volume V and at the proximal portion 120, so as not to occlude the area underlying the inside of the front opening 111.

The present invention therefore allows to achieve the proposed objects, allowing a high flexibility of use with high precision by virtue of the versatile support of the laser head.

The invention claimed is:

1. A device (1) for inspecting a cavity of a patient, comprising:

a retractor body (100) extending along a longitudinal axis (X) between a distal end (101) and a proximal end (102);

a handle (200) applied or fixed to the proximal end (102) of the retractor body (100);

an adapter body (300);

wherein the retractor body (100) has a distal portion (110) having a substantially tubular shape and a proximal portion (120) extending from the distal portion (110) in a diverging fashion, wherein the distal portion (120) defines a retraction zone of an internal cavity of a patient and internally delimits an internal volume (V) accessible from a rear access opening (130) made on the proximal portion (120), wherein said distal portion (110) of the retractor body (100) has at least one front (111) and/or lateral opening (140) to allow access to the mucosa or tissue of the patient from said internal volume (V); and wherein said adapter body (300) is removably applicable, in use, to said retractor body (100) and in particular to said proximal portion (120);

characterized in that it further comprises at least one support seat (500) arranged on the adapter body (300) and configured to supportingly receive a front surface (610) of a laser head (600), wherein said at least one support seat (500) is made on an auxiliary body (400) stably applicable to the adapter body (300), in particular directly connectable to the adapter body (300).

2. The device according to claim 1, wherein said at least one support seat (500) is arranged on the adapter body (300) in such a position as to be, in use, axially spaced from the proximal portion (120) and opposite the distal portion (110).

3. The device according to claim 1, wherein said at least one support seat (500) is rigidly connected to the adapter body (300), in particular integrally made with the adapter body (300).

4. The device according to claim 1, wherein said at least one support seat (500) is arranged in a radially external position with respect to an external profile of the adapter body (300).

5. The device according to claim 1, wherein said at least one support seat (500) is arranged in a radially internal position with respect to an external profile of the adapter body (300).

6. The device according to claim 1, wherein said at least one support seat (500) is arranged at an external profile of the adapter body (300).

7. The device according to claim 1, wherein the auxiliary body (400) has a pair of arms (410) and a connection portion fixed to the two arms (410), at least one of the two arms (410) having a respective support seat (500) and the arms (410) being configured to embrace opposite sides of the adapter body (300).

8. The device according to claim 7, wherein the arms (410) each have at least one curved portion (411) defining a concavity and are oriented with the concavities facing each other, preferably said support seat (500) being arranged on a respective curved portion (411).

9. The device according to claim 7, wherein the adapter body (300) has a first, front end (301) provided with means for reversible connection to the retractor body (100), in particular to the proximal portion (120), and a second rear end, opposite the first and preferably provided with means for connection to an operating accessory, in particular to a camera, and wherein the auxiliary body (400) is configured for the sliding application to the second end of the adapter body (300) up to an application position arranged in an intermediate position between said first and second ends, preferably with snap-fitted locking.

10. The device according to claim 9, wherein said auxiliary body and adapter body have guide means to facilitate a controlled sliding of the auxiliary body (400) on the adapter body (300), preferably said guide means comprising one or more linear guides.

11. The device according to claim 1, wherein said proximal portion and said adapter body (300) define therebetween at least one lateral window for accessing the internal volume (V) and wherein said window is arranged at said support seat and/or at a segment joining the support seat and the front and/or lateral opening of the distal portion.

12. The device according to claim 1, wherein said support seat (500) is defined by a stop wall (510) in the shape of a spherical cap having a central opening (520), and wherein said central opening (520) has an axis (a), defined by joining the centre of the central opening (520) and the centre of the support seat (500) having a spherical cap shape, inclined by an acute angle with respect to said longitudinal axis of the retractor body (100).

13. The device according to claim 12, wherein said support seat (500) further has a conical-shape lateral containment wall (530), defining a pair of generatrices passing through the centre of the stop wall (510) in the shape of a spherical cap.

14. The device according to claim 1, comprising two support seats (500) arranged on opposite sides with respect to the longitudinal axis (X), in particular in symmetrical positions with respect to a longitudinal plane of symmetry of the retractor body (100).

15. The device according to claim 1, wherein said at least one support seat (500) is directly or indirectly connected to the retractor body (100) through a hinge connection;

said support seat (500) being reversibly movable from an operative position, in which the support seat is close to the proximal portion (102), to an inoperative position, in which the support seat (500) is close to the handle (200).

16. The device according to claim 15, wherein said support seat is movable from the operative position to the inoperative position and vice versa due to a rotation around the hinge connection.

* * * * *